United States Patent [19]

Baltz et al.

[11] Patent Number: 4,935,340
[45] Date of Patent: Jun. 19, 1990

[54] METHOD OF ISOLATING ANTIBIOTIC BIOSYNTHETIC GENES

[75] Inventors: Richard H. Baltz; R. Nagaraja Rao, both of Indianapolis; Richard K. Stanzak, Poland; Patti J. Treadway, Greenwood, all of Ind.

[73] Assignee: Eli Lilly and Company, Indianapolis, Ind.

[21] Appl. No.: 742,349

[22] Filed: Jun. 7, 1985

[51] Int. Cl.$^5$ .................. C12Q 1/68; C12P 19/34; C12N 15/00; C12N 1/20; C07H 21/04
[52] U.S. Cl. .......................... 435/6; 435/91; 435/172.3; 435/252.35; 536/27; 935/11; 935/14; 935/16; 935/75; 935/78; 935/79; 935/80
[58] Field of Search .............. 435/6, 91, 172.1, 172.3, 435/243, 253, 320, 886, 252.3, 252.31–252.35; 935/29, 11, 14, 16, 72, 75, 78, 79, 80; 536/27

[56] References Cited

PUBLICATIONS

Thompson et al; Nature 286: 525, (1980).
Isreali–Reches et al; Mol. Gen. Genet. 194: 362, (1984).
Grunstein et al; Proc. Natl. Acad. Sci. USA 72: 3961, (1975).
Murakami et al; Chem. Abstr. 100: 1505p, (1984), of J. Antibiotic, 36(10), 1305, (1983).
Hopwood; in Biochemistry and Genetic Regulation of Commercially Important Antibiotics, 1983, Vining (ed.), Addison-Wesley Publishing Co., Reading, MA, pp. 1–23.
Chater, 1984, *Microbial Development,* Streptomyces Differentiation, R. Locisk and L. Shapiro, eds., Cold Spring Harbor Laboratories, 1984, pp. 89–115.
Kirby et al., 1975, Nature 254 (5497):265.
Kirby and Hopgood, 1977, J. Gen. Microbiol. 98:239.
Gil and Hopwood, 1983, Gene 25:119.
Rhodes et al., 1984, Biochem. Soc. Trans. 12:586.
Feitelson and Hopwood, 1983, Mol. Gen. Genet. 190:394.
Jones and Hopwood, 1984, J. Biol. Chem. 259(22):14151.
Malpartida and Hopwood, 1984, Nature 309:462.
Murakami et al., 1984, Abstract from the Annual Meeting of the Society of Fermentation Technology of Japan.
McGraw-Hill Newswatch, Oct. 7, 1985, at 3.
Murakami et al., Mol. Gen. Genet. (1986), 205:42–50.
Stanzak et al., Biotechnology (1986), 4:229–232.

*Primary Examiner*—James Martinell
*Attorney, Agent, or Firm*—Amy E. Hamilton; Leroy Whitaker

[57] ABSTRACT

The present invention is a method for isolating antibiotic biosynthetic genes. To practice the method, an antibiotic resistance-conferring DNA segment is labelled and used as a probe to find, via DNA hydridization, homologous DNA in a genetic library which comprises chromosomal and plasmid DNA of an antibiotic-producing organism. Individual vectors of the genetic library which hybridize to the antibiotic resistance-conferring gene, and which comprise ~1–45 kb of contiguous DNA from the antibiotic-producing organism, which also comprise an antibiotic biosynthetic gene. The present method is exemplified by using the erythromycin resistance-conferring gene of *Streptomyces erythreus* to clone the erythromycin biosynthetic pathway from the same organism. The erythromycin biosynthetic pathway isolated with the present method synthesizes erythromycin when introduced into *S. lividans* TK23.

16 Claims, 2 Drawing Sheets

METHOD OF ISOLATING ANTIBIOTIC BIOSYNTHETIC GENES

SUMMARY OF THE INVENTION

The present invention is a method for isolating antibiotic biosynthetic genes. The present method is most useful when used to isolate antibiotic biosynthetic pathways, which are the entire set of antibiotic biosynthetic genes necessary for the biosynthesis of a particular antibiotic. Antibiotic biosynthetic genes can be used to enhance antibiotic production, to produce novel antibiotics, and to isolate other antibiotic biosynthetic genes.

The present method is especially useful in isolating antibiotic biosynthetic genes from Streptomyces, organisms which provide over one-half of the clinically significant antibiotics. Because of the resulting commercial significance of Streptomyces, much time and effort has been expended in the study of Streptomyces genetics and the development of Streptomyces cloning vectors and transformation systems. Consequently, much is now known about Streptomyces, and several cloning vectors exist transforming the organism. However, the methods of recombinant DNA technology have not been readily applied to Streptomyces because of the difficulty of isolation of antibiotic biosynthetic genes.

In contrast, the present invention provides a novel method that will have great impact on the production of antibiotics by fermentation. The present method makes use of the linkage of antibiotic resistance-conferring genes with antibiotic biosynthetic genes. Linkage describes the distance between two or more genes. Two genes are closely linked when the two genes are close together on the same chromosome or are present on the same plasmid. The linkage between antibiotic biosynthetic and resistance-conferring genes can be utilized to isolate antibiotic biosynthetic genes for purposes of improving antibiotic-producing organisms or producing novel antibiotics.

Prior to the present invention, antibiotic biosynthetic genes were difficult to isolate. Prior art methods required that a diverse set of mutants be constructed from the antibiotic-producing organisms from which antibiotic biosynthetic genes were to be isolated. The mutants, called "blocked mutants," had to be defective for an antibiotic biosynthetic gene. These mutants were difficult to isolate and characterize. Once the mutants were obtained, they were transformed with cloned DNA from genetic libraries, and the transformants were analyzed to determine if the "block" had been complemented by the transforming DNA. The method was time consuming, because each transformant had to be screened for enzyme activity or antibiotic production, as there were no other methods to tell which recombinant vectors of the genetic library had DNA segments that comprised an antibiotic biosynthetic gene.

The present invention is a method for using antibiotic resistance-conferring genes to identify segments of DNA that comprise antibiotic biosynthetic genes. Many species that produce antibiotics also produce enzymes that catalyze reactions that confer resistance to those antibiotics. Antibiotic resistance-conferring genes can now be isolated by gene cloning. For instance, cloning DNA from a Streptomyces strain that produces a given antibiotic into a Streptomyces strain normally sensitive to that antibiotic can yield transformants which contain the antibiotic resistance-conferring gene. The clone containing the antibiotic resistance-conferring gene can be isolated by selection for resistance to the antibiotic. One embodiment of the present method consists of isolating antibiotic resistance-conferring genes on large segments of DNA, so that the antibiotic biosynthetic genes linked to the resistance-conferring genes are also cloned.

However, not all antibiotic biosynthetic genes from antibiotic-producing organisms can be isolated by the above-described method. Nevertheless, the linkage between antibiotic resistance-conferring genes and antibiotic biosynthetic genes can still be used to isolate antibiotic biosynthetic genes in the majority of cases. Because of the structural similarity that exists between members of a given class of antibiotics, the antibiotic resistance-conferring genes for a given class of antibiotics will often have similar DNA sequence and encode similar enzymatic activity. Because of this similar DNA sequence, also called homology, one antibiotic resistance-conferring gene for an antibiotic of a given class can be used to identify DNA segments comprising another antibiotic resistance-conferring gene for that same class. If the DNA segments are of the proper size, antibiotic biosynthetic genes linked to the resistance-conferring gene will also be identified. The DNA segments can be of any reasonable size, allowing the isolation of a single antibiotic biosynthetic gene with a relatively small segment or the isolation of an entire antibiotic biosynthetic pathway with a relatively large segment.

The antibiotic biosynthetic gene-comprising DNA segments can be cloned onto any of the available cloning vectors for a particular organism. Inserting the biosynthetic genes into multi-copy vectors, such as plasmids, and introducing those vectors into the hosts from which the genes were isolated can result in increased antibiotic production. Introducing a vector which comprises an entire antibiotic biosynthetic pathway into hosts which produce no antibiotic, but which recognize the transcriptional and translational control signals of the pathway genes, results in the production of the antibiotic in the transformed host. Introducing the same vector into hosts which produce an antibiotic different from the one produced by the host from which the biosynthetic genes were isolated can result in the production of a novel antibiotic.

For purposes of the present invention, as disclosed and claimed herein, the following terms are defined below.

AmR - the apramycin resistance-conferring gene.

Antibiotic - a substance produced by a microorganism which, either naturally or with limited chemical modification, will inhibit the growth of or kill another microorganism or eukaryotic cell.

Antibiotic Biosynthetic Gene - a DNA segment that encodes an enzymatic activity which is necessary for an enzymatic reaction in the process of converting primary metabolites into antibiotics.

Antibiotic Biosynthetic Pathway - the entire set of antibiotic biosynthetic genes necessary for the process of converting primary metabolites into antibiotics.

Antibiotic-Producing Organism - any organism, including, but not limited to, Actinoplanes, Actinomadura, Bacillus, Cephalosporium, Micromonospora, Penicillium, Nocardia, and Streptomyces, which either produces an antibiotic or contains genes which, if expressed, would produce an antibiotic.

Antibiotic Resistance-Conferring Gene - a DNA segment that encodes an enzymatic or other activity which confers resistance to an antibiotic.

ApR - the ampicillin resistance-conferring gene.

Bifunctional Cloning Shuttle Vector - a recombinant DNA cloning vector which can replicate and/or integrate into organisms of two different genera.

Cloning - the process of incorporating a segment of DNA into a recombinant DNA cloning vector and transforming a host cell with the recombinant DNA.

cos - the lambda cohesive end sequence.

Cosmid - a recombinant DNA cloning vector which not only can replicate in a host cell in the same manner as a plasmid but also can be packaged into phage heads.

EryR - the erythromycin resistance-conferring gene.

Genetic Library - a set of recombinant DNA cloning vectors into which segments of DNA, comprising substantially all of the DNA of a particular organism, have been cloned.

Hybridization - the process of annealing two single-stranded DNA molecules to form a double-stranded DNA molecule, which may or may not be completely base-paired.

NmR - the neomycin resistance-conferring gene.

ori - a plasmid origin of replication.

Recombinant DNA Cloning Vector - any autonomously replicating or integrating agent, including, but not limited to, plasmids, comprising a DNA molecule to which one or more additional DNA molecules can be or have been added.

Restriction Fragment - any linear DNA molecule generated by the action of one or more restriction enzymes.

rRNA - ribosomal ribonucleic acid.

Sensitive Host Cell - a host cell that cannot grow in the presence of a given antibiotic without a DNA segment that confers resistance thereto.

Str ori - a Streptomyces plasmid origin of replication.

Transductant - a recipient host cell that has undergone transformation by recombinant phage infection.

Transformant - a recipient host cell that has undergone transformation.

Transformation - the introduction of DNA into a recipient host cell that changes the genotype and results in a change in the recipient cell.

DETAILED DESCRIPTION OF THE INVENTION

The present invention is a method for isolating antibiotic biosynthetic genes, said method comprising:

(1) isolating chromosomal and plasmid DNA from an antibiotic-producing organism;

(2) preparing a genetic library of said chromosomal and plasmid DNA, such that each recombinant vector of said library comprises a fragment of said DNA of a size ranging from ~1-45 kb;

(3) hybridizing an antibiotic resistance-conferring gene to said library;

(4) identifying which recombinant DNA cloning vectors of said library hybridize to said antibiotic resistance-conferring gene; and (5) isolating said hybridizing vectors from said library.

Each of the five steps of the present method are described more fully below.

Step one of the present method requires the isolation of chromosomal and plasmid DNA from an antibiotic-producing organism. A variety of methods for isolating Streptomyces chromosomal and plasmid DNA are well known in the art, and one such method is presented in Example 1, below. The method of Example 1 is generally applicable to all antibiotic-producing organisms, although some minor modifications, such as incubation time or reaction volume, may be necessary to optimize the procedure for a particular organism.

A variety of antibiotic-producing organisms and the antibiotics which those organisms produce are presented in Tables I–IX below. The present method is applicable to, but not limited to, all of the organisms listed in the Tables.

TABLE I

| Aminocyclitol Antibiotic-Producing Organisms | |
|---|---|
| Organism | Antibiotic |
| Bacillus | |
| various species | various aminocyclitols |
| Micromonospora | |
| various species | gentamycins |
| Saccharopolyspora | |
| various species | various aminocyclitols |
| Streptomyces | |
| albogriseolus | neomycins |
| albus var. metamycinus | metamycin |
| aquacanus | N-methyl hygromycin B |
| atrofaciens | hygromycins |
| bikiniensis | streptomycin |
| bluensis var. bluensis | bluensomycin |
| canus | ribosyl paromamine |
| catenulae | catenulin |
| chrestomyceticus | aminosidine |
| crystallinus | hygromycin A |
| erythrochromogenes var. narutoensis | streptomycin |
| eurocidicus | A16316-C |
| fradiae | hybrimycins and neomycin |
| fradiae var. italicus | aminosidine |
| galbus | streptomycin |
| griseus | streptomycin |
| griseoflavus | MA 1267 |
| hofuensis | seldomycin complex |
| hygroscopicus | hygromycins, leucanicidin, and hygrolidin |
| hygroscopicus forma glebosus | glebomycin |
| hygroscopicus var. limoneus | validamycins |
| hygroscopicus var. sagamiensis | spectinomycin |
| kanamyceticus | kanamycin A and B |
| Streptomyces | |
| kasuqaensis | kasugamycins |
| kasugaspinus | kasugamycins |
| lavendulae | neomycin |
| lividus | lividomycins |
| mashuensis | streptomycin |
| microsporeus | SF-767 |
| netropsis | LL-AM31 |
| noboritoensis | hygromycins |
| olivaceus | streptomycin |
| olivoreticuli var. cellulophilus | destomycin A |
| poolensis | streptomycin |
| rameus | streptomycin |
| ribosidificus | SF733 |
| rimofaciens | destomycin A |
| rimosus forma paromomycinus | paromomycins and |

TABLE I-continued

Aminocyclitol Antibiotic-Producing Organisms

| Organism | Antibiotic |
|---|---|
| | catenulin |
| spectabilis | spectinomycin |
| tenebrarius | tobramycin and apramycin |
| Streptoverticillium | |
| flavopersicus | spectinomycin |

TABLE II

Ansamycin Antibiotic-Producing Organism

| Organism | Antibiotic |
|---|---|
| Micromonospora | |
| various species | various ansamycins |
| Nocardia | |
| mediterranei | rifamycin |
| Streptomyces | |
| collinus | ansatrienes and napthomycins |
| diastochromogenes | ansatrienes and napthomycins |
| galbus subsp. griseosporeus | napthomycin B |
| hygroscopicus | herbimycin |
| hygroscopicus var. geldanus var. nova | geldamycin |
| nigellus | 21-hydroxy-25-demethyl 25-methylthioproto-streptovaricin |
| rishiriensis | mycotrienes |
| sp. E/784 | actamycin and mycotriene |
| sp. E88 | mycotrienes |
| spectabilis | streptovaricins |
| tolypophorous | tolypomycin |

TABLE III

Anthracycline and Quinone Antibiotic-Producing Organisms

| Organism | Antibiotic |
|---|---|
| Streptomyces | |
| caespitosus | mitomycins A, B, and C |
| coelicolor | actinorhodin |
| coeruleorubidicus | daunomycin |
| cyaneus | ditrisarubicin |
| flavogriseus | cyanocycline A |
| galilaeus | aclacinomycin A, auramycins, and sulfurmycins |
| lusitanus | napthyridinomycin |
| peuceticus | daunomycin and adriamycin |
| violochromoqenes | arugomycin |

TABLE IV

β-Lactam Antibiotic-Producing Organisms

| Organism | Antibiotic |
|---|---|
| Cephalosporium | |
| various species | various β-lactams |
| Nocardia | |
| lactamadurans | cephamycin C |
| Penicillium | |
| various species | various β-lactams |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, clavulanic acid, and other clavams |

TABLE IV-continued

β-Lactam Antibiotic-Producing Organisms

| Organism | Antibiotic |
|---|---|
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B |
| halstedi | cephamycin A and B |
| heteromorphus | C2081X and cephamycin A and B |
| hygroscopicus | deacetoxycephalosporin C |
| lipmanii | penicillin N, 7-methoxycephalosporin C, A16884, MM 4550, and MM 13902 |
| olivaceus | (MM 17880) epithienamycin F, MM 4550, and MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

TABLE V

Macrolide, Lincosamide, and Streptogramin Antibiotic-Producing Organisms

| Organism | Antibiotic |
|---|---|
| Micromonospora | |
| rosaria | rosaramicin |
| Streptomyces | |
| albireticuli | carbomycin |
| albogriseolus | mikonomycin |
| albus | albomycetin |
| albus var. coilmyceticus | coleimycin |
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| Streptomyces | |
| griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin A₃ and |

TABLE V-continued
Macrolide, Lincosamide, and Streptogramin Antibiotic-Producing Organisms

| Organism | Antibiotic |
| --- | --- |
| lavendulae | josamycin aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin A and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocyline |
| roseocitreus | albocycline |
| spinichromoenes var. suragaoensis | kujimycins |
| tendae | carbomycin |
| thermotolerans | carbomycin |
| venezuelae | methymycins |
| violaceoniger | lankacidins and lankamycin |

TABLE VI
Miscellaneous Antibiotic-Producing Streptomyces

| Antibiotic Type | Streptomyces Species | Antibiotic |
| --- | --- | --- |
| amino acid analogues | sp. | cycloserine |
| cyclopentane ring-containing | coelicolor | methylenomycin A |
|  | erythrochromogenes | sarkomycin |
|  | violaceoruber | methylenomycin A |
| nitro-containing | venezuelae | chloramphenicol |
| polyenes | griseus | candicidin |
|  | nodosus | amphotericin B |
|  | noursei | nystatin |
| tetracyclines | aureofaciens | tetracycline, chlortetracycline, demethyltetracycline, and demethylchlortetracycline |
|  | rimosus | oxytetracycline |

TABLE VII
Nucleoside Antibiotic-Producing Organisms

| Organism | Antibiotic |
| --- | --- |
| Corynebacterium |  |
| michiganese pv. rathayi | tunicamycin analogues |
| Nocardia |  |
| candidus | pyrazofurin |
| Streptomyces |  |
| antibioticus | ara-A |
| chartreusis | tunicamycin |
| griseoflavus var. thuringiensis | streptoviridans |
| griseolus | sinefungin |
| lysosuperificus | tunicamycin |

TABLE VIII
Peptide Antibiotic-Producing Organisms

| Organism | Antibiotic |
| --- | --- |
| Actinoplanes |  |
| missouriensis | actaplanin |
| teichomyceticus | teicoplanin |
| Bacillus |  |
| various species | bacitracin, polymixin, and colistin |
| Nocardia |  |
| candidus | A-35512 and avoparcin |
| lurida | ristocetin |
| orientalis | vancomycin |
| Streptomyces |  |
| antibioticus | actinomycin |
| aureus | thiostrepton |
| canus | amphomycin |
| eburosporeus | LL-AM374 |
| haranomachiensis | vancomycin |
| pristinaespiralis | pristinamycin |
| roseosporus | lipopeptides, such as A21978C |
| toyocaensis | A47934 |
| virginiae | A1030 |

TABLE IX
Polyether Antibiotic-Producing Organism

| Organism | Antibiotic |
| --- | --- |
| Actinomadura |  |
| various species | various polyethers |
| Dactylosporangium |  |
| various species | various polyethers |
| Nocardia |  |
| various species | various polyethers |
| Streptomyces |  |
| albus | A204, A28695A and B, and salinomycin |
| aureofaciens | narasin |
| cacaoi var. asoensis | lysocellin |
| chartreusis | A23187 |
| cinnamonensis | monensin |
| conglobatus | ionomycin |
| eurocidicus var. asterocidicus | laidlomycin |
| flaveolus | CP38936 |
| gallinarius | RP 30504 |
| griseus | grisorixin |
| hygroscopicus | A218, emericid, DE3936, A120A, A28695A and B, etheromycin, and dianemycin |
| lasaliensis | lasalocid |
| longwoodensis | lysocellin |
| mutabilis | S-1173a |
| ribosidificus | lonomycin |
| violaceoniger | nigericin |
| Streptoverticillium |  |
| various species | various polyethers |

After isolating the chromosomal and plasmid DNA from a particular antibiotic-producing organism, the present method requires the construction of a genetic library of the prepared DNA. There are many methods of preparing genetic libraries, and so long as certain size constraints described herein are met, any of those methods can be used in the present method. A preferred method of constructing a Streptomyces genetic library has been disclosed and claimed in U.S. patent application Ser. No. 06/655,178, filed 9/27/84, Docket No. X-6422 and the continuation-in-part application of Ser. No. 655,178, which is U.S. patent application Ser. No. 06/742,172, filed 6/7/85, Docket No. X-6422A. The aforementioned method is preferred, because very large segments of DNA, ~30–45 kb, can be incorporated into the cosmid cloning vectors disclosed and claimed in the aforementioned application. Using this preferred method increases the likelihood that an entire antibiotic biosynthetic pathway will be cloned. This preferred method is illustrated in Example 2 below.

The various methods of constructing genetic libraries primarily differ with respect to the restriction enzyme and/or molecular linkers used to prepare the chromosomal and plasmid DNA for insertion into the recombinant DNA cloning vector used to construct the library. Ideally, several libraries are constructed from each antibiotic-producing species, with each library constructed with chromosomal and plasmid DNA prepared for insertion into the recombinant DNA cloning vector with a different restriction enzyme and/or molecular linker. Preparing a variety of libraries in this manner will minimize the risk of cutting, and thereby possibly destroying, a particular antibiotic biosynthetic gene during the construction of the library.

Genetic libraries also differ on the average size of the chromosomal and plasmid DNA inserted into the recombinant DNA cloning vector used to construct the library. As stated above, larger inserts are desired so that entire biosynthetic pathways can be cloned. One method of controlling the size of a DNA insert is to carefully monitor digestion of large DNA fragments. As a general rule, the longer the digestion time, the smaller the resulting digestion products, until complete digestion is obtained.

DNA can also be fragmented by a variety of mechanical, as opposed to enzymatic, techniques. Mechanical methods usually require that the DNA be modified by the addition of DNA linkers to the DNA or by treatment to make the DNA blunt-ended after the fragmentation process.

The construction of a genetic library is also governed by the choice of the recombinant DNA cloning vector used to construct the library. The preferred recombinant DNA cloning vector of the present invention is able to replicate in both *E. coli* and Streptomyces. Such a bifunctional cloning vector, also called a "shuttle vector," allows manipulation of the antibiotic biosynthetic gene-containing DNA in *E. coli*, an organism eminently suited for the manipulation of DNA, and introduction of the antibiotic biosynthetic gene-containing DNA into Streptomyces without construction of numerous intermediate recombinant DNA cloning vectors. Preferred recombinant DNA cloning vectors for the construction of genetic libraries for use in the method of the present invention are disclosed in the aforementioned U.S. patent application Ser. No. 655,178 and the continuation-in-part application of Ser. No. 655,178, Ser. No. 06/742,172, Docket No. X-6422A these vectors are pKC420, pKC427, pKC428, pKC448, pKC462, pKC462A and pKC467.

However, the present method is not limited to the use of a particular recombinant DNA cloning vector. A great number of cloning vectors exist that are suitable for the purposes of the present invention, such as, for example, *E. coli*-Streptomyces shuttle vectors disclosed in U.S. Pat. Nos. 4,416,994; 4,343,906; 4,477,571; 4,362,816; and 4,340,674. Nor is the present invention limited to the use of bifunctional vectors or to bifunctional vectors of *E. coli* and Streptomyces, because bifunctional vectors between *E. coli* and an antibiotic-producing organism such as Bacillus, Cephalosporium, or Penicillium, for example, would be equally useful.

The present method can also be executed using monofunctional vectors, such as, for example, plasmid pBR322, the Charon phages, phage ΦC31, plasmid SCP2, plasmid SCP2*, plasmid pIJ702, and derivatives of these vectors.

After the genetic library is constructed, segments of DNA known to confer antibiotic resistance are first labelled and then brought into contact with the genetic library under conditions that allow complementary strands of DNA to anneal. This annealing process, or hybridization, is an important step of the present invention and a variety of important factors are critical to successful execution of this step. Because the resistance-conferring gene functions as a probe that seeks out and identifies segments of chromosomal and/or plasmid DNA containing antibiotic biosynthetic genes, the selection of a particular antibiotic resistance-conferring DNA segment is an important factor in the present method.

In an especially preferred embodiment of the present invention, the resistance-conferring gene used in the present method confers resistance to the antibiotic produced by the organism from which the chromosomal or plasmid DNA has been isolated. For example, acetyltransferases, adenylyltransferases, phosphotransferases, and methyltransferases can confer resistance to the aminocyclitol antibiotics. Thus, using a DNA segment that encodes an acetyltransferase, adenylyltransferase, phosphotransferase, or methyltransferase in the present method to identify aminocyclitol biosynthetic gene-containing DNA segments is a preferred embodiment of the present invention. Not all aminocyclitol-producing organisms will contain the same type of aminocyclitol resistance-conferring gene. Thus, it may be necessary to use a variety of resistance-conferring genes before successfully isolating an aminocyclitol biosynthetic gene-containing DNA fragment.

Macrolide, lincosamide, and streptogramin antibiotic-producing organisms often contain antibiotic resistance-conferring genes such as methyltransferases. In fact, most rRNA methyltransferases confer resistance to a wide variety of macrolide, lincosamide, and streptogramin antibiotics and are therefore called "MLS resistance determinants." Therefore, a preferred embodiment of the present invention comprises the use of a DNA segment encoding a methyltransferase to identify macrolide, lincosamide, and streptogramin biosynthetic gene-containing DNA segments.

It is especially important to note that the present method provides a means to isolate antibiotic biosynthetic gene from organisms which have been only poorly characterized genetically. Because antibiotic resistance genes from different species often show homology, and indeed, some scientists believe many organisms possess antibiotic resistance-conferring genes through the action of trans-poson-like elements (Israeli-Reches et al., 1984, Mol. Gen. Genet. 194:362), the present method can be used to isolate antibiotic biosynthetic genes from a species of a genus that is distinct from the genus from which the antibiotic resistance-conferring gene was isolated.

No resistance-conferring genes are known to exist for some of the antibiotics listed in the preceding Tables. However, the present invention is not limited to a particular antibiotic resistance-conferring gene. Instead, the present method describes how to use any antibiotic resistance-conferring gene to identify antibiotic biosynthetic genes. Therefore, even should antibiotic resistance-conferring genes be discovered after the filing date of the present invention, the present invention comprises the use of those novel resistance-conferring genes in the present method.

Furthermore, the present method can be used to isolate antibiotic biosynthetic genes from organisms which produce antibiotics for which no resistance-conferring gene is known. In such an embodiment of the present invention, the chromosomal and plasmid DNA of the organism is hybridized to resistance-conferring genes specific for antibiotics other than those the organism is known to produce. Some organisms possess silent or cryptic antibiotic biosynthetic genes (Jones et al., 1984, J. Biol. Chem. 259: 14158). These silent genes could not only be linked to the organism's active biosynthetic genes, but also could possess a resistance-conferring gene, specific for the antibiotic that the silent pathway could produce. Furthermore, the unknown resistance-conferring gene for the antibiotic the organism does produce could be homologous to a known resistance-conferring gene. In either case, the present invention can be used to isolate antibiotic biosynthetic genes from organisms that produce antibiotics for which no resistance-conferring gene is known.

A great many resistance genes are known. The following table, Table X, presents many, but not all, of the known resistance-conferring genes and provides citations to the references that disclose the genes. Depository accession numbers in Table X refer to either the strain or the plasmid from which the resistance-conferring gene can be isolated. The ATCC is the American Type Culture Collection, located in Rockville, Md. 20852. The NRRL is the Northern Regional Research Center, Agricultural Research Service, U. S. Department of Agriculture, located in Peoria, Ill. 61604.

| Resistance-Conferring Gene | Organism Comprising Gene | Plasmid Comprising Gene | Depository Accession Number | Reference to Article Describing the Resistance-Conferring Gene |
|---|---|---|---|---|
| ANTIBIOTIC RESISTANCE-CONFERRING GENES | | | | |
| hygromycin B: phosphotransferase | E. coli JR225 | pKC203 | ATCC 31912 | Kaster et al., 1983, Nucleic Acids Research 11(19): 6895 |
| kanamycin and neomycin: phosphotransferase | E. coli/Tn5 | pKC7 | ATCC 37084 | Beck et al., 1982, Gene 19:327 |
| neomycin: acetyltransferase | Streptomyces fradiae | PIJ1 and PIJ4 | ATCC 10745 | Thompson et al., 1980, Nature 286:525 Thompson et al., 1982, Gene 20:51 |
| thiostrepton: rRNA methylase | Streptomyces azureus | pIJ5 and pIJ6 | ATCC 14921 | Thompson et al., 1980, Nature 286:525 Thompson et al., 1982, Gene 20:51 |
| kanamycin: phosphotransferase | Streptomyces fradiae | pIJ2 and pIJ3 | ATCC 10745 | Thompson et al., 1980, Nature 286:525 Thompson et al., 1982, Gene 20:51 |
| viomycin: phosphotransferase | Streptomyces vinaceus | pIJ36 | No deposit | Thompson et al., 1982, Gene 20:51 |
| erythromycin: rRNA methyltransferase | Streptomyces erythreus | pIJ43 | ATCC 39156 | Thompson et al., 1982, Gene 20:51 |
| apramycin: acetyltransferase | E. coli. | pKC309 | NRRL B-15827 | U.S. Pat. application Ser. No. 06/655,180, filed 09/27/84 |
| tylosin: rRNA methyltransferase | Streptomyces fradiae | pSVB2 | NRRL 15880 | U.S. Pat. Application Ser. No. 06/653,975, filed 09/25/84 |
| spiramycin: rRNA methyltransferase | Streptomyces ambofaciens | pNAS105 | NRRL B-15919 | U.S. Pat application Ser. No. 06/685,677, filed 12/24/84 |
| methylenomycin | Streptomyces coelicolor 19332 | pSCP111, pSLP111, and pSLP112 | No deposit | Bibb et al., 1980, Nature 284: 526 |
| penP: β-lactamase | Bacillus licheniformis | pTB2 | No deposit | Neugebauer et al., 1981, Nucl. Acids Res. 9:2577 Gray and Chang, 1981, J. Bacteriol. 145:422 |
| erythromycin: ermD, a rRNA methyltransferase | Bacillus licheniformis | pBD90 | No deposit | Gryczan et al., 1984, Mol. Gen. Genet. 194:349 |
| erythromycin: ermC, a rRNA methyltransferase | Staphylococcus aureus | pEI94 | No deposit | Shivakumar and Dubnau, 1981, Nucl. |

As stated above, the present invention is not limited to a particular set of antibiotic resistance-conferring genes. Methods of isolating antibiotic resistance-conferring genes are well known in the art. One such method is described in Thompson et al., 1980, Nature 286:525. Methods for isolating antibiotic resistance-conferring genes, such as the method of Thompson et al., usually involve cloning DNA from an antibiotic-producing organism and transforming the cloned DNA into a second organism that is sensitive to the antibiotic the first organism produces. Transformants of the second organism that are resistant to the antibiotic are presumed to comprise an antibiotic resistance-conferring gene.

Although the above method is primarily an effective way to clone antibiotic resistance-conferring genes, the method can be adapted, by keeping the cloned sequences large enough so that genes flanking the antibiotic resistance-conferring gene are also cloned on the same DNA segment as the antibiotic resistance-conferring gene to clone antibiotic biosynthetic genes. Therefore, the present method also comprises isolating an antibiotic resistance-conferring gene of an organism in order to obtain the antibiotic biosynthetic genes linked or adjacent to that antibiotic resistance-conferring gene.

When using a resistance-conferring gene, such as one of the genes listed in the preceding Table, in the present method, it is desirable to label only the protein-coding sequence, or some subfragment thereof, of the gene to use for identification of an antibiotic biosynthetic gene-comprising DNA segment. Of course, not all of the antibiotic resistance-conferring genes in the preceding Table have been sequenced, so the exact boundaries of the protein-coding sequence of those genes are unknown. However, it is still possible to eliminate any extraneous DNA that is not necessary to confer resistance before using the antibiotic resistance-conferring gene in the present method.

The purpose of using only the protein-coding sequence of the antibiotic resistance-conferring gene in the present method is to prevent hybridization of DNA sequences adjacent to the antibiotic resistance-conferring gene from hybridizing with homologous sequences present in the chromosomal or plasmid DNA from which antibiotic biosynthetic genes are to be isolated. Because these flanking sequences might not be specific to antibiotic resistance-conferring genes or antibiotic biosynthetic genes, the presence of these sequences could lead to false positives if the sequences were present during the hybridization step of the present method. However, if the vector on which the antibiotic resistance-conferring gene is present is not homologous to the chromosonal or plasmid DNA from which the antibiotic biosynthetic genes are to be isolated, the presence of those vector sequences will not impair the successful operation of the present method.

In order to identify any antibiotic resistance-conferring DNA that hybridizes with the chromosomal or plasmid DNA of an antibiotic-producing organism, the antibiotic resistance-conferring DNA must be labelled. Usually, this labelling of the DNA is done through techniques which cause radioactive molecules, such as radioactive phosphorous ($^{32}P$) or deoxyribonucleotides comprising $^{32}P$, to be incorporated into the DNA. One such method of labelling DNA through the use of radioactive deoxyribonucleotides is presented in Example 3. Another method of labelling DNA involves biotinylation of the DNA; this method is described and marketed by Bethesda Research Laboratories (Gaithersburg, Md. 20877) and works well in the method of the present invention. The present invention is not limited to a particular method of labelling the antibiotic resistance-conferring gene.

After the antibiotic resistance-conferring gene has been labelled, the resistance-conferring gene is brought into contact with the chromosomal or plasmid DNA from the antibiotic-producing organism under conditions which allow single strands of the antibiotic resistance-conferring gene DNA to anneal with homologous regions of the single-stranded chromosomal or plasmid DNA of the antibiotic producing organism. This annealing process is called hybridization; the process is described in more detail in Example 4.

After the hybridization reaction, the unannealed, labelled DNA is washed from the system. Various parameters of the wash, also described in Example 4, can be adjusted to set the degree of homology required for a labelled DNA to remain annealed. In the method of the present invention, the washes are controlled such that the labelled DNA must be at least 50% homologous to the chromosomal and plasmid DNA of the antibiotic-producing organism before it will not be washed out of the system.

The labelled DNA which remains in the system is bound to the chromosomal and plasmid DNA of the antibiotic producing organism which, in turn, is bound to a substrate, usually nitrocellulose. The substrate-bound DNA is produced by culturing the organisms comprising the aforementioned genetic library on a material such as nitrocellulose; lysing the organisms under conditions that denature the DNA of the organisms which becomes bound to the nitrocellulose in single-stranded form; and, finally, treating the nitrocellulose-bound DNA to conditions, such as prolonged heat, that cause the DNA to become covalently bound to the nitrocellulose. In this manner, the DNA of the antibiotic-producing organism becomes bound to a substrate in a single-stranded form such that hybridization with the antibiotic resistance-conferring DNA can readily occur.

Other systems for preparing the DNA of the antibiotic-producing organism for hybridization involve a material, such as nylon-based membranes or Whatman chromatography paper, to which the DNA is bound by becoming intertwined with the fibers of which the material is made. Before or during hybridization, however, the DNA must be denatured into single strands, so that the antibiotic resistance-conferring DNA can hybridize with it.

The actual system used for immobilizing and denaturing the DNA of the antibiotic-producing organism in no way limits the method of the present invention. A variety of techniques exist or are possible for binding the DNA of a genetic library to a substrate in such a manner that hybridization with a labelled antibiotic resistance-conferring DNA segment can take place so that specific vectors of the genetic library that hybridize can be identified. The method of the present invention is not limited to any particular method or set of methods for accomplishing the hybridization step.

The system used for immobilizing and denaturing the DNA of the antibiotic-producing organism must allow for subsequent identification of those recombinant vectors in the genetic library which comprise sequences to which the antibiotic resistance-conferring DNA hybridizes. Usually, this goal is accomplished by culturing the hosts comprising the recombinant vectors of the genetic library on a master plate, which is specially marked or shaped. Replicas of this master plate set of cultures are then made, preferably on the material which will be used to bind the DNA comprised in the genetic library. The replicas are marked such that cultures on the replica plate can be identified with the cultures on the master plate from which they arose; the markings on, or shape of, the master plate are for aiding this purpose. The replica plates are then used for the purposes of the present invention. The master plate is preserved, with its cultures intact and viable, so that after recombinant vectors of the genetic library which comprise antibiotic biosynthetic genes are identified, the organisms comprising those recombinant vectors can be isolated and cultured.

Recombinant vectors comprising antibiotic biosynthetic genes are identified in accordance with method used to label the antibiotic resistance-conferring DNA. If a method employing the radioactive labelling of the DNA was used, identification will proceed by measuring the radioactivity preserved on the material which binds the genetic library DNA after the hybridization and washing steps. Radioactivity can be conveniently measured by exposing X-ray film to the material bound to the genetic library DNA (the "filters") after the hybridization and washing steps. Other methods, such as those employing scintillation or geiger counters, can also be employed in the present method. When the biotinylation method is used, the filters are exposed to dyes which allow vectors that hybridized to the antibiotic resistance-conferring gene to be identified by colorimetric means.

Once a recombinant vector of a genetic library from an antibiotic-producing organism has been shown to comprise sequences which are homologous to and hybridize with DNA sequences from an antibiotic resistance-conferring gene, it then becomes necessary to identify the antibiotic biosynthetic genes which are linked to the antibiotic resistance-conferring homologous sequences and which are also present on the plasmid. A variety of methods exist for identifying the presence and type of antibiotic biosynthetic genes on a vector; the methods are briefly summarized below.

The presence of an antibiotic biosynthetic pathway on a recombinant DNA cloning vector can be determined by introducing the recombinant vector into hosts which do not naturally produce an antibiotic but which recognize the control signals of the pathway genes and replication functions of the recombinant vector. Presence of an antibiotic pathway, or at least a regulator of a cryptic pathway, on the recombinant vector is indicated by the production of an antibiotic by the transformed organism, because the untransformed organism produces no antibiotic. Alternatively, the pathway-comprising recombinant vector could be introduced into an organism that does produce an antibiotic, and presence of a novel antibiotic pathway, or of at least antibiotic biosynthetic genes, would be indicated by the production of an antibiotic not produced by the untransformed organism.

The presence of antibiotic biosynthetic genes on a recombinant DNA cloning vector can also be identified by the transformation of antibiotic blocked mutants to wild-type state with the recombinant vector. Furthermore, the presence and type of antibiotic biosynthetic genes can also be determined by enzyme assays, such as those described by Seno and Baltz, 1981, Antimicrobial Agents and Chemotherapy 20(3):370.

The Example section, below, is presented to illustrate the method of the present invention. The Examples illustrate the use of the erythromycin resistance-conferring gene, which is thought to encode a ribosomal RNA methyltransferase, of plasmid pIJ43 to identify erythromycin biosynthetic genes in accordance with the method of the present invention. Not only did the erythromycin resistance-conferring gene hybridize, in a specific manner, to the chromosomal and plasmid DNA of several erythromycin or other antibiotic-producing organisms, but also the erythromycin resistance-conferring gene was used in the method of the present invention to identify a recombinant vector shown to encode the antibiotic pathway for erythromycin which drives expression of erythromycins in a host that when untransformed produces no useful antibiotic. Thus, the Examples illustrate the utility of the present invention and the general applicability of the present invention to antibiotic-producing organisms.

EXAMPLE 1

Isolation of *Streptomyces erythreus* Chromosomal and Plasmid DNA

*Streptomyces erythreus* produces a variety of related compounds called erythromycins (erythromycin A–F and erythronolide). The erythromycins are commercially significant antibiotics which are produced by fermentation. Cloning the erythromycin biosynthetic genes could lead to recombinant DNA cloning vectors which could enhance the production of erythromycins from *S. erythreus* fermentations. This example describes the isolation of *S. erythreus* chromosomal and plasmid DNA.

About 250 ml of Trypticase soy broth containing 50 μg/ml erythromycin were inoculated with a culture of *Streptomyces erythreus* (NRRL 2338), and the culture was incubated at 30° C. for 24 hours. The culture was harvested by centrifugation, and the cell pellet was resuspended in 20 ml of a solution that was 15% in sucrose; 25 mM in Tris-HCl, pH=8; and 25 mM in EDTA. One hundred μl of 100 mg/ml lysozyme were added to this cell mixture, which was then incubated at 37° C. for eight minutes. After the lysozyme treatment, 200 μl of 10 mg/ml proteinase K and 750 μl of 20% SDS were added to the cell mixture, which was then incubated at 70° C. for eight minutes.

After the 70° C. incubation, the cell mixture was cooled on ice, added to 1.5 ml of 10 M KOAc, and then incubated on ice for 30 minutes. The cell mixture was then extracted once with TE-saturated phenol (TE is a buffer comprising 10 mM Tris-HCl, pH=7.5, and 1 mM EDTA) and centrifuged to separate the aqueous phase from the phenol. The aqueous phase of the phenol extraction was extracted once with Sevag, a mixture of chloroform and isoamyl alcohol at a ratio of 24:1, respectively. After centrifugation of the Sevag extraction, the aqueous layer was added to and mixed with two volumes of 100% ethanol.

Upon the addition of the ethanol, the DNA precipitated and became visible as a white material in the solution. By gently swirling the solution, the long strands of DNA became interwound and formed a very loose pellet of DNA. The loose pellet of DNA was removed from the solution, and the DNA was washed with five ml of 70% ethanol. The DNA was then placed in a tube containing two ml of TE buffer, and the tube was placed on a roller drum overnight. The roller-drum provided enough gentle agitation so that the DNA dissolved but did not shear to any appreciable extent.

One hundred μl of RNAse A (2 mg/ml) were added to the two ml of chromosomal and plasmid DNA, and the mixture was incubated at 37° C. for thirty minutes. The mixture was extracted twice with TE-saturated phenol and then extracted twice with Sevag. After the final Sevag extraction, four ml of absolute ethanol were added to the aqueous phase, and the DNA precipitated out of solution as before. The DNA was washed with five ml of 70% ethanol, air dried, and resuspended in one ml of TE buffer. About 5–10 mg of *Streptomyces erythreus* DNA were obtained by this procedure. The average size of the DNA fragments in the solution was about ~70 kb.

The above method is applicable to Streptomyces and other antibiotic-producing prokaryotes. A general method for isolating fungal DNA is presented by Tudzynski and Esser, 1982, Current Genetics 5:227.

EXAMPLE 2

Construction of a Genetic Library Comprising *Streptomyces erythreus* Chromosomal and Plasmid DNA A. Description of Cosmid Shuttle Vector pKC462A U.S. patent application Ser. No. 06/655,180, Docket No. X-6422, filed 9/27/84, and the continuation-in-part application of Ser. No. 655,180 Ser. No. 06/742,172, Docket No. X-6422A, filed 6/7/85, describe a number of cosmids, which are *E. coli*-Streptomyces shuttle vectors useful in constructing genetic libraries. The present Example details the construction of a *Streptomyces erythreus* genetic library with the aid of cosmid shuttle vector pKC462A, a vector disclosed in the aforementioned continuation-in-part Application. Cosmid shuttle vector pKC462A can be isolated from *E. coli* K12 SF8/pKC462A, which has been deposited with the NRRL under the accession number NRRL B-15973.

The isolation of cosmid shuttle vector pKC462A from *E. coli* K12 SF8/pKC462A is disclosed in Example 11 of the aforementioned continuation-in-part U.S. patent application, said Example 11 is incorporated herein by reference.

Figure 1:
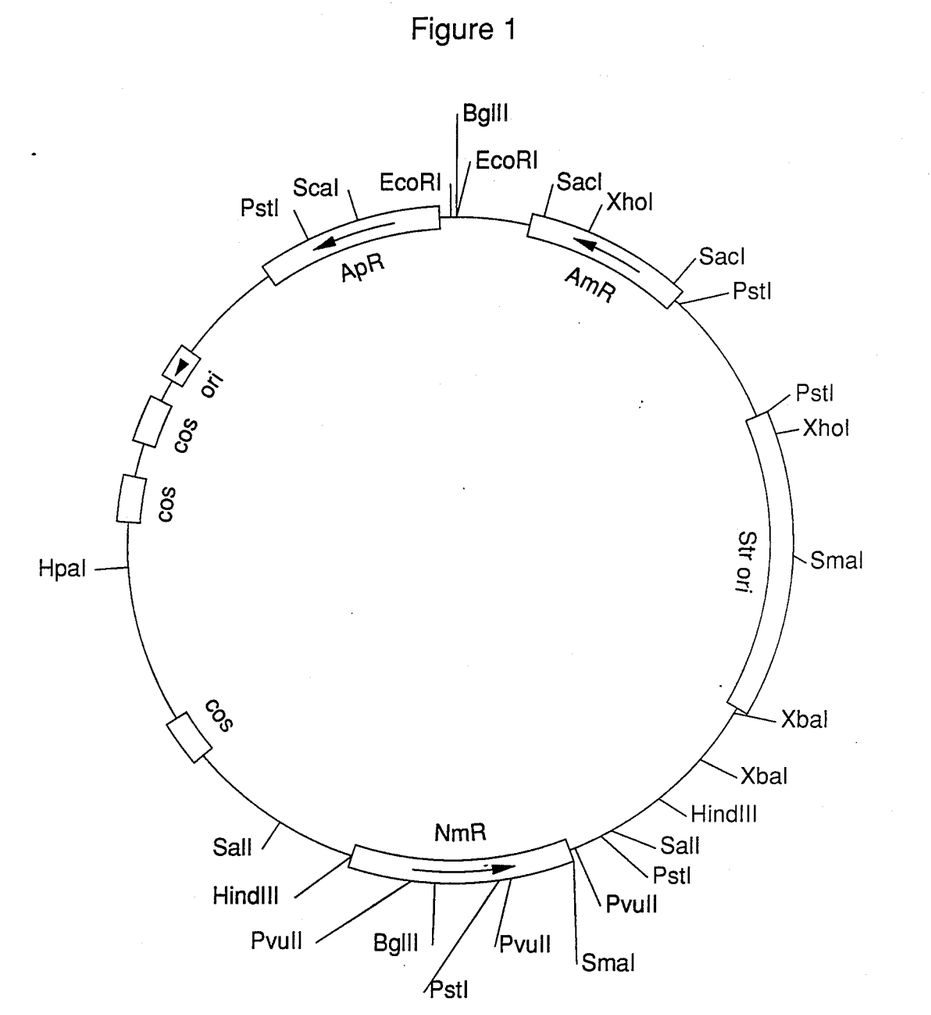
FIG. 1. Restriction Site and Function Map of Plasmid pKC462A.
Figure 2:
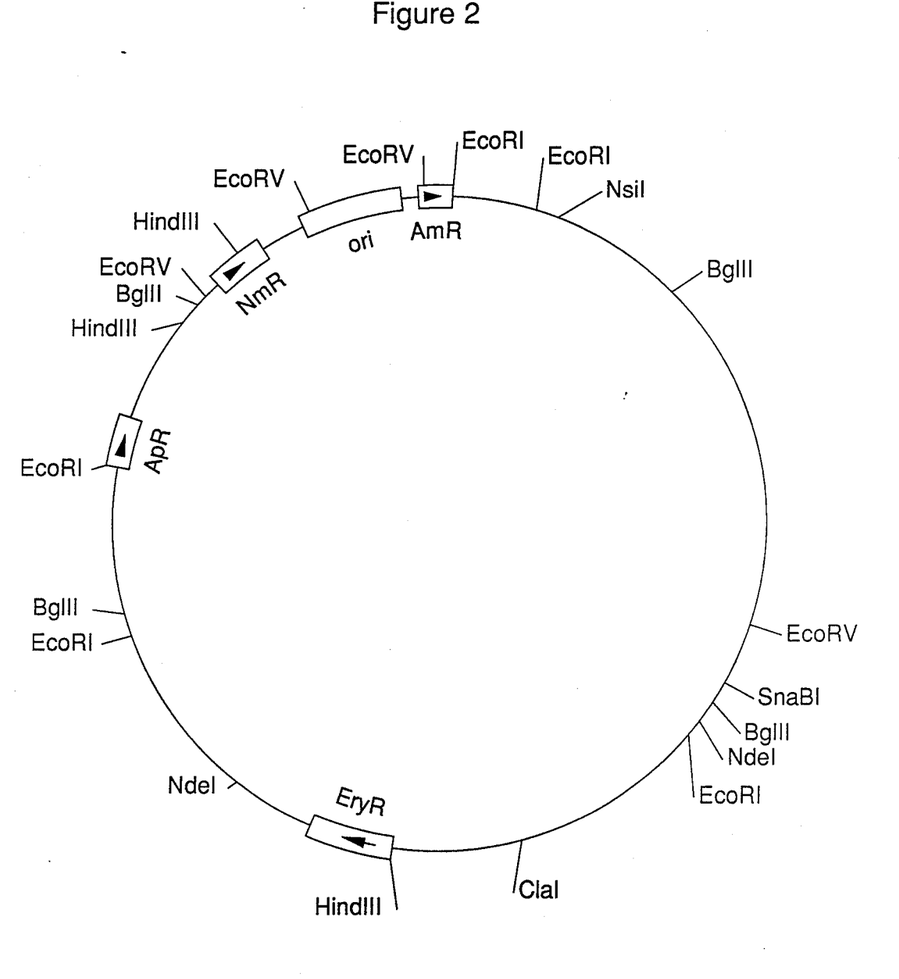
FIG. 2. Restriction Site and Function Map of Plasmid pKC488.

A restriction site and function map of cosmid pKC462A is presented in FIG. 1 of the accompanying drawings.

B. Preparation of the Cosmid DNA

About 50 μg of cosmid pKC462A DNA were digested in 500 μl of 1X HpaI buffer (20 mM KCl; 10 mM Tris-HCl, pH=7.4; 10 mM MgCl$_2$; and 1 mM dithiothreitol (DTT)) with 100 units of HpaI restriction enzyme for 3 hours at 37° C. About 50 μl of 10X BAP (bacterial alkaline phosphatase) buffer (500 mM Tris-HCl, pH=8, and 500 mM NaCl) and 2.5 units of BAP (International Biotechnologies, Inc., P.O. Box 1565, New Haven, Conn. 06506) were added to the HpaI-digested DNA, and the resulting reaction was incubated for one hour at 70° C. After extracting the BAP-treated DNA with phenol and then Sevag, the DNA was precipitated with ethanol. The DNA was then digested in 500 μl of 1X BamHI buffer (150 mM NaCl; 6 mM Tris-HCl, pH=7.9; 6 mM MgCl$_2$; and 100 μl/ml bovine serum albumin (BSA)) with 90 units of BamHI restriction enzyme for 3 hours at 37° C. The DNA was again extracted with phenol and Sevag, precipitated with ethanol, and dissolved in 50 μl of TE buffer.

C. Preparation of the Insert DNA

About fifty μg of the *Streptomyces erythreus* DNA prepared in Example 1 were incubated with 30 units of MboI in 500 μl of 1X MboI buffer (100 mM NaCl; 10 mM Tris-HCl, pH 7.4; 10 mM MgCl$_2$; and 1 mM DTT) at 37° C. for 15 minutes. This particular incubation time was found, empirically, to give the desired partial fragmentation, leaving DNA fragments of ~30–45 kb in size. The MboI-digested DNA was extracted with phenol and Sevag and then dissolved in 50 μl of TE buffer.

About 25 μg of the MboI-digested *Streptomyces erythreus* DNA were subsequently treated with BAP (1.25 units for the first hour at 70° C. and then an additional 1.25 units for another hour at 70° C.) in 100 pl of 1X BAP buffer. The BAP-treated DNA was extracted with phenol and Sevag, precipitated with ethanol, and then dissolved in 50 μl of TE buffer. The size of this DNA was estimated on a 0.3% agarose gel and was found to be ~30–45 kb.

D. Ligation of the Vector DNA to the Insert DNA

About 125 ng of the pKC462A DNA prepared in Example 2B were mixed with 500 ng of the MboI-digested *Streptomyces erythreus* DNA prepared in Example 8B and then ligated with 400 units (New England Biolabs, Beverly, Mass. 01915) of T4 DNA ligase in 20 μl of 1X ligase buffer (50 mM Tris-HCl, pH=7.7; 10 mM MgCl$_2$; 20 mM DTT; and 50 μg/ml BSA) made 1 mM in ATP. The ligation reaction was incubated 16 hours at 16° C. and was terminated by heating at 70° C. for 10 minutes.

E. In Vitro Packaging

Packaging was performed by adding about 10 μl of the ligation mixture (~62.5 ng of hybrid vector DNA) to Biotec packaging kit (Promega Biotec, 2800 S. Fish Hatchery Road, Madison, Wis. 53711) at 30° C. for 1 hour. About 500 μl of 0.1 M NaCl; 0.01M Tris-HCl, pH=8; and 0.01M MgSO$_4$ were added to the mixture after the packaging reaction. Chloroform, about 25 μl, was also added to the mixture to kill bacteria.

F. Transduction of *E. coli* K12 SF8

About 200 μl of the packaged cosmids prepared in Example 2E (25 ng of vector DNA) were adsorbed to 500 μl of *E. coli* strain K12 SF8 (NRRL B-15835) grown to an O.D. 550 of about 0.7 in TY broth (10 g tryptone and 5 g yeast extract per liter) supplemented with 0.2% maltose and 10 mM magnesium sulfate. After the cells were washed in 10 ml of a solution 10 mM in Tris-HCl, pH=8.0, and 10 mM in MgCl$_2$, adsorption was done at 37° C. for 10 minutes in 10 mM Tris-HCl, pH=8.0, and 10 mM MgSO$_4$ After adsorption, the *E. coli* K12 SF8 cells were grown in 5 ml of TY broth for one hour at room temperature, and transductants were selected at 30° C. on plates containing 200 μg/ml of apramycin. Approximately 4000 colonies resulted from the plating of the transduced cells, which results in a transduction efficiency of about $1 \times 10^4$ transductants per microgram of recombinant vector DNA.

About twenty-five hundred transductants were picked from the plates and placed, one transductant per well, in 96-well microtiter dishes containing TY broth with 100 μg/ml ampicillin. The microtiter dishes were incubated at 37° C. overnight. These microtiter dishes served as the master plates of the genetic library of *Streptomyces erytheus* DNA and were stored at ~4° C. throughout the remainder of the experiment.

EXAMPLE 3

Preparation of Nitrocellulose Filters for Hybridization

The 26 microtiter dishes containing ~2500 individual isolates of the *Streptomyces erythreus* genetic library were replica-plated onto nitrocellulose in duplicate. Each plate was individually replica-plated onto a section of nitrocellulose, hereinafter referred to as a filter. The filters were marked so that it was possible to tell from which master plate the filter was taken and the orientation of the filter with respect to the master plate from which it originated.

The filters were then placed, transductant-side up, onto TY-agar plates containing 100 μg/ml ampicillin, and the plates on which the filters were placed were incubated at 37° C. overnight.

The following morning the filters were placed on blotting paper saturated with 0.5 M NaOH for five minutes. After blotting the filters to dryness, this five minute incubation on 0.5 M NaOH-saturated blotting paper was repeated. The filters were again blotted to dryness and then placed, for five minutes, on blotting paper saturated in 1 M Tris-HCl, pH=8. The filters were again blotted to dryness and then placed, for five minutes, on blotting paper saturated in a solution of 1.5 M Tris-HCl, pH=8, and 3.0 M NaCl. The filters were air dried and then baked at 80° C. for two hours under vacuum. The foregoing process lyses the cells, denatures the DNA once contained in the cells, and irreversibly binds the single-stranded DNA to the nitrocellulose filters. The above-described process prepares the filters for hybridization.

EXAMPLE 4

Construction of Plasmids pKC407 and pKC408

Plasmids pKC407 and pKC408 were constructed to have a vector with the following features: (1) presence of the *Streptomyces erythreus* erythromycin resistance-conferring gene; (2) presence of *S. erythreus* DNA other than that DNA necessary to confer erythromycin resistance kept to a minimum; and (3) presence of only well-characterized DNA on the plasmid. Plasmid pIJ43 does not meet the above requirements; consequently, plasmids pKC407 and pKC408 were constructed.

A. Culture of *E. coli* K12 803/pIJ43 and Isolation of Plasmid pIJ43.

A 5 ml culture of *E. coli* K12 803/pIJ43 (ATCC 39156) was grown in TY media (1% tryptone; 0.5% yeast extract; and 0.5% sodium chloride, pH=7.5) containing 100 μg/ml ampicillin according to conventional microbiological procedures. The cells were collected in a table-top centrifuge, and the cell pellet was resuspended in 1 ml of a solution (Solution I) that was 0.3 M sucrose, 25 mM EDTA (ethylene diaminetetraacetic acid), and 25 mM Tris-HCl, pH=8.0. The cells were transferred to an Eppendorf tube and centrifuged for about one minute, and the pellet was resuspended in 0.5 ml of Solution I. About 50 μl of freshly-made lysozyme (20 mg/ml in water) were added to the resuspended cells, and the solution was incubated at 37° C. for 10 minutes.

After the addition of 250 μl of freshly-made lysis mix (2% sodium dodecyl sulfate and 0.3 N NaOH), the lysed cells were immediately and completely vortexed. The cells were then incubated for ten minutes at 50° C., cooled, and added to 100 μl of phenol-Sevag (phenol-chloroform-isoamyl alcohol in a ratio of 25:24:1, respectively). After the extraction mixture was centrifuged for two minutes in an Eppendorf centrifuge, the supernatant was decanted and transferred to another tube along with 70 μl of unbuffered 3 M sodium acetate and 0.7 ml of isopropanol to precipitate the DNA. This solution was incubated for five minutes at room temperature and then centrifuged for two minutes. The supernatant was gently and completely decanted.

The DNA precipitate was dissolved in 500 μl of TE buffer (10 mM Tris-HCl, pH=8.0, and 1 mM EDTA) and 25 μl of 100 mM spermine-HCl was added. This mixture was vortexed, incubated for five minutes at room temperature, and then centrifuged for five minutes in an Eppendorf centrifuge. The supernatant was again completely decanted and discarded, and the precipitated DNA was vortexed with 1 ml of a solution comprised of 75% ethanol, 0.3 M sodium acetate, and 10 mM magnesium acetate. This solution was incubated for five minutes at room temperature, and the DNA was collected as above. The resulting DNA pellet was dissolved in 10 μl of TE buffer.

B. Isolation of the ~1.8 kb BamHI-PstI Restriction Fragment of Plasmid pIJ43.

About 5 μg of the plasmid pIJ43 prepared in Example 4A were digested in 1X BamHI buffer (150 mM NaCl; 6 mM Tris-HCl, pH=7.9; 6 mM MgCl₂; and 1 mM dithiothreitol) in a total volume of 50 μl with 10 units (New England Biolabs) each of BamHI and PstI restriction endonucleases. The reaction mixture was incubated at 37° C. for about two hours. The reaction was terminated by extraction with phenol and Sevag. The BamHI-PstI-digested plasmid pIJ43 DNA was precipitated with ethanol, dried, and then dissolved in 5 μl of TE buffer. The DNA was electrophoresed on a 0.5% agarose gel until the desired ~1.8 kb BamHI-PstI restriction fragment was separated from the other digestion fragments. Whatman DEAE cellulose paper was placed in a slit located ahead of the desired DNA band, and the desired fragment of DNA was electrophoresed onto the DEAE paper. The DEAE paper was washed with 1 ml of TE buffer, and the DNA was eluted off of the DEAE paper with 400 μl of TE buffer adjusted to 1 M in NaCl. The eluted DNA was ethanol precipitated, and the purified fragment obtained was dissolved in 5 μl of TE buffer.

About 2 μg of the ~1.8 kb BamHI-PstI restriction fragment of plasmid pIJ43 were obtained by this procedure. This ~1.8 kb fragment comprises the erythromycin resistance-conferring gene.

C. Preparation of BamHI-PstI - Digested Plasmid pEMBL9+

Plasmid pEMBL9+ is a plasmid disclosed in Dente et al., 1983, Nucleic Acids Research 11:1645. The plasmid comprises the pBR322-derived β-lactamase gene and a multiple cloning site and is about 4 kb in size. Although plasmid pEMBL9+ was used in the actual exemplification of the present method, a wide variety of plasmids exist that would have been equally suitable for the purposes of the present invention. Essentially, the present method requires that if the entire plasmid which comprises the antibiotic resistance-conferring gene is to be labelled and used in the hybridization reaction, all of the sequences other than the antibiotic resistance-conferring gene must not be homologous to the DNA being examined for the presence of antibiotic biosynthetic genes. Plasmid pEMBL9+ was therefore selected because of its multiple cloning site and its *E. coli* plasmid-derived sequences. Other plasmids which would have been equally suitable for the purposes of the present invention are numerous: plasmid pUC4K (NRRL B-15836); plasmid pUC8, which is commercially available from Bethesda Research Laboratories (BRL), and plasmid pUC9, which is also available from BRL.

All of these plasmids, pEMBL9+, pUC4K, pUC8, and pUC9, encode the β-galactosidase α-fragment constructed so as to comprise a multiple cloning site. When these plasmids are transformed into host cells which correctly complement the α-fragment, such as is the case when *E. coli* K12 RR1ΔM15 (NRRL B-15440) is the transformed host cell, the cells express β-galactosidase and will turn indicator plates containing 5-bromo-4-chloro-3-indolyl-β-D-galactoside (x-gal) and isopropylthio-β-galactoside (IPTG) a blue color. Both x-gal and IPTG are available from BRL. If, however, a fragment of DNA is cloned into the multiple cloning site of these plasmids such that the coding sequence for the a-fragment is interrupted, the transformants will not express β-galactosidase activity, and the plate will not exhibit the blue color. Thus, these α-fragment-encoding plasmids present a convenient way of identifying recombinant plasmids.

Host cells transformed with plasmid pMEBL9+ were treated in accordance with the method of Example 4A, and ~5 μg of plasmid pEMBL9+ DNA were isolated. The plasmid pMEBL9+ DNA was then digested with restriction enzymes BamHI and PstI in substantial accordance with the procedure of Example 4B. The digested DNA was not purified by gel electrophoresis. Instead, the BamHI-PstI digested plasmid pEMBL9+ DNA was resuspended in 5 μl of TE buffer.

D. Ligation and Construction of *E. coli* K12 PR1ΔM15/pKC407

About 1 μg each of the BamHI-PstI-digested plasmid pEMBL9+ DNA prepared in Example 4C and the ~1.8 kb BamHI-PstI restriction fragment prepared in Example 4B were ligated in 20 μl of 1X ligase buffer (50 mM Tris-HCl, pH=7.8; 10 mM MgCl$_2$; 20 mM dithiothreitol; and 1 mM ATP) with 400 units of T4 DNA ligase (New England Biolabs) for 16 hours at 16° C. The reaction was terminated by incubation at 70° C. for 10 minutes. After cooling on ice, the resulting ligated DNA was used to transform E. coli K12 RR1ΔM15 (NRRL B-15440) according to the procedure of Maniatis et al., 1982, Molecular Cloning, Cold Spring Harbor Laboratory, Cold Spring Harbor, N.Y., which is incorporated herein by reference.

The identity of the desired transformants was confirmed by plating the cells on TY-agar plates containing 1 mM IPTG, 20 μg/ml x-gal, and 50 μg/ml ampicillin and also by restriction analysis of the plasmid DNA of the transformants. β-galactosidase-negative transformants harboring plasmid pKC407 DNA were cultured and their plasmid DNA isolated in substantial accordance with the procedure of Example 4A. The plasmid pKC407 DNA, which comprises the erythromycin resistance-conferring gene, was labelled and used in the method of the present invention.

EXAMPLE 5

Labelling of Plasmid pKC407

This Example describes a process whereby one strand of a double-stranded DNA molecule is first removed and then replaced. This process is often called "nick-translation." Because the process is carried out in the presence of deoxycytidine 5'-[α-$^{32}$P] triphosphate ($^{32}$P-dCTP), and because each strand of the DNA molecule comprises deoxycytidyl residues, the replacement reaction incorporates radioactive phosphorous, $^{32}$P, into the DNA. This radioactivity aids in the identification step of the present invention, which is that step in which vectors of the genetic library which have hybridized to an antibiotic resistance-conferring DNA segment are identified.

Five μg of plasmid pKC407 DNA were digested with restriction enzymes BamHI and PstI in 200 μl of 1X BamHI buffer, and the resulting ~1.8 kb BamHI-PstI restriction fragment was isolated in substantial accordance with the procedure of Example 4B. About 2.5 μg of the desired ~1.8 kb restriction fragment were isolated and suspended in 5μl of TE buffer.

The nick-translation was carried out by first dissolving 1.0 μg of the ~1.8 kb BamHI-PstI restriction fragment of plasmid pKC407 in the following mixture: 5 μg of 10X nick-translation buffer (0.5 M Tris-HCl, pH=7.8; 0.05 M MgCl$_2$; and 0.1 M β-mercaptoethanol); 5μl of a solution 300 μM in deoxyguanidine triphosphate (dGTP), deoxyadenosine triphosphate (dATP), and thymidine triphosphate (TTP); 2 μl (20μCi) of $^{32}$P-dCTP, from Amersham (2636 S. Clearbrook Dr., Arlington Heights, Ill. 60005); and 48μl of H$_2$O. The reaction was begun by diluting a 1 mg/ml solution of beef pancreatic, ribonuclease-free deoxyribonuclease (DNAse), from Miles Laboratories (P.O. Box 2000, Elkhart, Ind. 46515), by 10,000 fold and then immediately adding 1 μl of the diluted DNAse to the mixture containing the plasmid pKC407 DNA. The reaction was incubated at 15° C. for two minutes, and then, 1 μl (10 units) of E. coli DNA polymerase I (New England Biolabs) was added to the reaction, which was incubated at 15° C. for two hours.

The reaction was stopped by the addition of 50 μl of 0.1 M EDTA and an incubation at 65° C. for ten minutes. The reaction mixture was then passed through a Sephadex G-100 (Sigma Chemical Co., P.O. Box 14508, St. Louis, Mo. 63178) column in a 10 ml disposable pipette, with elution buffer composed of 10 mM Tris-HCl, pH=7.5; 1 mM EDTA; 0.1 M NaCl; and 0.01% SDS. The plasmid pKC407 DNA was monitored with a Geiger counter as it passed through the column. The reaction typically incorporated $10^7$ counts per minute per microgram of DNA. The labelled DNA was stored at −70° C. until use.

EXAMPLE 6

Hybridization of the Radioactively-Labelled Erythromycin Resistance-Conferring Gene to Filters Comprising a *Streptomyces Erythreus* Genetic Library and Identification of the Hybridizing Vectors A. Pre-hybridization and Hybridization The 52 filters prepared in Example 3 were submerged in 10 ml of pre-hybridization mixture, a solution of the following composition: 50% deionized formamide; 0.1% SDS; 10 mM HEPES, pH=6.9; 1.0 mM EDTA; 0.75 M NaCitrate; 0.75 M NaCl; 0.02% Ficoll, of molecular weight of 400,000; 0.02% polyvinylpyrrolidone; and 0.02% BSA. The filters were submerged in the pre-hybridization mixture for four hours at a temperature of 37° C.

After the pre-hybridization, the labelled plasmid pKC407 DNA prepared in Example 5 was incubated at 100° C. for five minutes and then immediately added to 27 ml of pre-hybridization mixture to yield the hybridization mixture. The filters were then removed from the prehybridization mixture and, in groups of six or less, were submerged in 3 ml aliquots of the hybridization mixture and incubated at 42° C. overnight.

During this incubation, the labelled DNA hybridizes to the genetic library located on the filters. Increasing the percent formamide in the hybridization mixture or increasing the temperature of incubation will increase the homology required for the labelled DNA to bind to recombinant vectors of the genetic library on the filter. These two variables, percent formamide and temperature of hybridization, serve as controls in the method of the present invention and allow for the selection of homology between the antibiotic resistance-conferring gene and the genetic library DNA to be in the desired 50–100% homology range.

After the overnight incubation, the filters were gently washed in 300 ml of a solution composed of 0.75 M NaCitrate, 0.75 M NaCl, and 0.2% SDS. The wash solution was kept at a temperature of about 65° C. The wash was repeated twice and the filters were then placed for two hours at room temperature in 300 ml of a solution composed of 0.3 M NaCitrate and 0.3 M NaCl. The filters were air-dried at room temperature.

The wash step provides further controls for selecting the homology between the antibiotic resistance-conferring gene and the vectors of the genetic library. Increased wash temperatures or decreased salt concentrations increase the amount of homology required for the labelled DNA to anneal to the vectors of the genetic library. Thus, varying the salt concentration or temperature of the wash solution allows the homology to be varied so as to be in the 50–100% range required by the method of the present invention.

B. Identification

The air-dried filters were wrapped in clear plastic and placed on sheets of cardboard, and Kodak (Rochester, N.Y. 14650) XAR-5 film was placed on top of the filters. The manipulations were carried out in a darkroom. A Lightning-Plus ® intensifying screen (Dupont DeNemours & Co., Inc., Photoproducts Dept., Wilmington, Del. 19898) was placed in the proper orientation on top of the film. The film was marked so that it could later be oriented with respect to the filters over which it was placed. The film, filters, and intensifying screen were then placed in a light-tight box and incubated at −70° C. for 2 hours. The incubation, or exposure, time can be varied to give the proper amount of exposure for any given experiment.

After the film was developed, dark spots appeared wherever labelled pKC407 DNA bound to a recombinant vector of the genetic library, which was in turn bound to the filters. These spots could be identified to a particular well of the master plate, because of the special care taken to mark each master plate, corresponding filters, and X-ray film. The use of duplicate filters helped to eliminate false positives. Three clones of the 2500 total gave strong positive results.

Recombinant clones, which were shown by the filters to comprise DNA which hybridized to the antibiotic resistance-conferring gene, were picked from the master plate, cultured, and subjected to the procedure of Example 4A in order to isolate their cosmid DNA. This cosmid DNA was then examined for the presence of antibiotic biosynthetic genes. One of the three cosmids, designated pKC488, has been extensively analyzed. Cosmid pKC488 is available from the NRRL in *E. coli* K12 SF8 under accession number NRRL B-18459.

EXAMPLE 7

Analysis of Cosmid pKC48B for the Presence of Antibiotic Biosynthetic Genes

A. Transformation of *Streptomyces lividans* TK23 and Expression of Antibiotic Activity

*Streptomyces lividans* TK23 does not produce any clinically significant antibiotics; although it does produce a pigment, actinorhodin, with weak antibiotic activity. Furthermore, *S. lividans* TK23 is sensitive to erythromycin. Consequently, *S. lividans* TK23 was selected as a good host for examining the cosmids identified in Example 6 for both the presence of an erythromycin resistance-conferring gene and also the presence of antibiotic biosynthetic genes. Because the origin of the cloned DNA in cosmid pKC488 was *S. erythreus*, any antibiotic biosynthetic genes present on the plasmids were expected to be erythromycin biosynthetic genes.

*Streptomyces lividans* TK23 can be obtained in lyophil form from the NRRL under the accession number NRRL 15826. The lyophilized cells are put into 10 ml of trypticase soy broth (TSB) (BBL, Cockeysville, Md. 21030) and incubated at 30° C. in a gyratory water bath (New Brunswick, Edison, N.J. 08817) at 240–260 rpm for 1–3 days. The incubation period should end when a Klett (Klett Manufacturing Co., Inc., New York, N.Y. 10028) reading of the culture is about 7–10 Klett units. A portion of the culture is then put on modified R2-agar plates (Baltz and Matsushima, 1981, J. Gen. Microbiol. 127:137) and incubated at 30° C. until sporulation occurs, usually after about a three day incubation. The spores are collected and suspended in water at a concentration of about $10^8$–$10^9$ spores/ml.

About 0.1 ml of this spore suspension was inoculated into 10 ml of TSB supplemented with 10.3% sucrose and 0.5% glycine. The culture was sonicated in a Branson ultrasonic water bath (Branson Cleaning Equipment Co., Shelton, Conn.) for one minute to disperse the spores. The culture was then incubated in a gyratory water bath at 240–260 rpm at 29° C. for 60–65 hours. The culture was homogenized in a Teflon pestle tissue grinder (A. H. Thomas Co., Philadelphia, Pa. 19105) and then sonicated for one second at 76 watts using a Branson model W185 sonifier.

The sonicated cells were collected by centrifugation (~2400 rpm) and resuspended in 10 ml of P medium (Baltz, 1978, J. Gen. Microbiol. 107:93). This procedure was repeated twice, but the last resuspension was done using P medium which contained 1 mg/ml, 3X crystalline, egg-white lysozyme (Calbiochem, LaJolla, Calif. 92037). The cell suspension was incubated at 4° C. for one hour. The resulting protoplasts were collected and washed twice with 10 ml of P medium per wash. The protoplasts were finally resuspended in 10 ml of P media.

In a separate tube, 0.8 μg of calf thymus DNA in 4 μl, of average size of about 5 kb, was mixed with 1.5 μg of protamine sulfate in 1.5 μl (Calbiochem). One μg of pKC488, brought to a final volume of 10 μl using P media, was added to the calf thymus DNA-protamine sulfate mixture. Two hundred μl of protoplasts and 500 μl of filter-sterilized, 55% PEG 1000 (Sigma) in P media were then added to the calf thymus DNA-protamine sulfate solution. After mixing, the contents of the tube were incubated at room temperature for one minute. The resulting transformed protplasts were then diluted 1:10, 1:100, and 1:1000 in P medium, and 100 μl of each dilution were individually plated in a soft-agar overlay on modified R2-agar plates in substantial accordance with the procedure of Baltz and Matsushima, 1981, J. Gen. Microbiology 127:137.

The plates were incubated at 29° C. for 16–24 hours. Then, a second soft-agar overlay was added to the plates which contained enough apramycin or erythromycin to give final concentrations, after diffusion, of 25 μg/ml apramycin or 200 μg/ml erythromycin. The plates were put at 29° C. and incubated until colonies could be seen. Recombinant vector pKC488 transformed *Streptomyces lividans* TK23 to apramycin and erythromycin resistance.

B. Analysis of *Streptomyces lividans* TK23/pKC488 Transformants for Expression of Antibiotic Activity 1. Plate-Plug Assay

*Streptomyces lividans* TK23/pKC488 transformants were cultured on R2-agar plates containing 25 μg/ml apramycin until the colonies were 5–10 millimeters in diameter. The colonies were then plugged and the plugs transferred, using a sterile transfer tube (Spectrum Medical Industrial, Inc., Los Angeles, CA 90054) to trypticase soy agar (TSA) plates which had been overlayed with soft-agar nutrient broth (Difco Laboratories, Detroit, Mich. 48232) containing *Micrococcus luteus* X160 (ATCC 9341). The plates were incubated at 34° C. for 16–24 hours. *Micrococcus luteus* (ATCC 9341) is sensitive to erythromycin A, B, C, D, and E and resistant to apramycin. Consequently, this *M. luteus* strain cannot grow around a plug which contains Streptomyces which are secreting erythromycin. In the plate-plug assay done with the *S. lividans* TK23/pKC488, there were clear zones of inhibition of *M. luteus* growth around the plugs of *S. lividans* TK23/pKC488. These zones of inhibition indicated the transformants were producing erythromycin.

2. Preparation of Extracts for Chromatography and Bioautography

The plugs prepared in Example 7(B)(1) were ground to paste in a Teflon pestle tissue grinder containing 1 ml of TSB, which had a pH=8 due to the addition of 100 μl of 1 N NaOH. An equal volume of methanol (MeOH) was added to and mixed with the paste, and the resulting mixture was incubated at room temperatures for 15–30 minutes. The mixture was centrifuged briefly to pellet the agar debris, and the supernatant was concentrated 5X by evaporation at room temperature.

3 Chromatography

Paper chromatography systems are preferred for good separation of erythromycin factors. Paper chromatography as performed on the concentrated extracts prepared in Example 7(b)(2) on Whatman #1 paper or on aluminum-backed cellulose plates (EM Reagents, DC - Alufolien Cellulose Art. 552). The bioactivity obtained upon bioautography of the developed chromatograms comigrated with erythromycin A standard (erythromycin D co-migrates with erythromycin A) in all of the solvent systems tested: (a) 1% v/v methylisobutylketone, and 0.5% $NH_4OH$ in distilled water; (b) 17.4 grams $K_2HPO_4$ and 30 ml ethanol per liter of distilled water; and (c) 7% w/v NaCl and 2.5% v/v methylethylketone in distilled water. Some transformants also produced factors which co-migrated with erythromycin precursors B and C.

4. Bioautography

The developed chromatograms were dried thoroughly in a fume hood for at least two hours. The chromatograms were then placed face down on *Micrococcus luteus* X160-seeded TSA plates for 30 minutes. The chromatograms were peeled off the plates and the plates were incubated at 34° for 16–24 hours. The chromatograms for the extracts prepared from *Streptomyces lividans* TK23/pKC488 transformants produced zones of inhibition resulting from substances on the chromatogram that comigrated with erythromycin A or its precursors, such as erythromycin B, C, or D, standards.

We claim:

1. A method for identifying and isolating an antibiotic biosynthetic gene linked to an antibiotic resistance-conferring gene, said method comprising identifying an antibiotic biosynthetic gene-containing DNA sequence, said DNA sequence not previously isolated, by hybridizing a labelled antibiotic resistance conferring-gene to said antibiotic biosynthetic gene-containing DNA and isolating said DNA thus identified.

2. The method of claim 1, which comprises:
   (1) isolating chromosomal and plasmid DNA from an antibiotic-producing organism;
   (2) preparing a genetic library of said chromosomal and plasmid DNA, such that the recombinant vectors of said library comprise a fragment of said DNA of a size ranging from ~1–45 kb;
   (3) hybridizing a labelled antibiotic resistance conferring gene to said library;
   (4) identifying which recombinant vectors of said library hybridize to said antibiotic resistance-conferring gene;
   (5) isolating said hybridizing vectors from said library.

3. The method of claim 1, wherein said DNA comprises the genes which encode the enzymes comprising an antibiotic biosynthetic pathway.

4. The method of claim 1, wherein said DNA is isolated from a species of a genus selected from the group of genera consisting of Actinomadura, Actinoplanes, Bacillus, Cephalosporium, Corynebacterium, Dactylosporangium, Micromonospora, Nocardia, Penicillium, Saccharopolyspora, Streptomyces, and Streptoverticillium.

5. The method of claim 4, wherein said genus is Streptomyces and said species is selected from the group consisting of albireticuli, ambofaciens, antibioticus, aureofaciens, cattleya, chartreusis, cinnamonensis, clavuligerus, erythreus, fradiae, hygroscopicus, kanamyceticus, lavendulae, macrosporeus, narbonensis, olivaceus, rimosus, tenebrarius, thermotolerans, toyocoensis, and virginiae.

6. The method of claim 5, wherein said species is erythreus.

7. The method of claim 5, wherein said species is fradiae.

8. The method of claim 1, wherein said antibiotic resistance-conferring gene confers resistance to an antibiotic selected from the group consisting of antibiotics apramycin, β-lactams, erythromycin, hygromycin, kanamycin, methelenomycin, neomycin, spiramycin, tobramycin, thiostrepton, tylosin, and viomycin.

9. The method of claim 1, wherein said antibiotic resistance-conferring gene encodes an enzymatic activity selected from the group consisting of acetyltransferase activity, β-lactamase activity, phosphotransferase activity, and rRNA methyltransferase activity.

10. The method of claim 8, wherein said antibiotic resistance-conferring gene confers resistance to erythromycin.

11. The method of claim 8, wherein said antibiotic resistance-conferring gene confers resistance to tylosin.

12. The method of claim 9, wherein said antibiotic resistance-conferring gene encodes rRNA methyltransferase activity.

13. The ~34 kb BglII fragment of plasmid pKC488.

14. A Streptomyces host cell transformed with plasmid pKC488.

15. The host cell of claim 14 that is *Streptomyces lividans*/pKC488.

16. A DNA sequence which encodes an enzyme in the erythromycin biosynthetic pathway, said DNA sequence being comprised on plasmid pK488.

* * * * *